United States Patent
Freeman

[11] Patent Number: 5,951,565
[45] Date of Patent: Sep. 14, 1999

[54] CORNEAL ENDOTHELIUM PROTECTIVE DEVICE

[75] Inventor: Jerre Minor Freeman, Memphis, Tenn.

[73] Assignee: Eagle Vision, Inc., Memphis, Tenn.

[21] Appl. No.: 08/949,445

[22] Filed: Oct. 14, 1997

[51] Int. Cl.$^6$ ............................................. A61F 9/00
[52] U.S. Cl. .................. 606/107; 606/166; 606/201; 623/4; 623/5; 623/6; 128/321
[58] Field of Search ................... 606/107, 166, 606/201; 623/4, 5, 6; 128/321

[56] References Cited

U.S. PATENT DOCUMENTS

| | | | |
|---|---|---|---|
| 4,387,706 | 6/1983 | Glass | 128/20 |
| 4,406,285 | 9/1983 | Villasenor et al. | 128/305 |
| 4,452,600 | 6/1984 | Schachar | 604/51 |
| 4,463,457 | 8/1984 | Kelman | 606/107 |
| 4,619,657 | 10/1986 | Keates et al. | 606/107 |
| 4,664,667 | 5/1987 | Kelman | 623/6 |
| 4,681,585 | 7/1987 | Sayano et al. | 623/6 |
| 4,759,763 | 7/1988 | Bissonette al. | 623/6 |
| 4,769,034 | 9/1988 | Poley | 623/6 |
| 4,819,631 | 4/1989 | Poley | 128/303 |
| 4,911,714 | 3/1990 | Poley | 623/6 |
| 4,917,680 | 4/1990 | Poley | 623/6 |
| 4,988,352 | 1/1991 | Poley | 606/107 |
| 4,990,150 | 2/1991 | Tsubota et al. | 606/107 |
| 5,021,057 | 6/1991 | Byrne, Jr. | 606/107 |
| 5,044,743 | 9/1991 | Ting | 351/163 |
| 5,078,742 | 1/1992 | Dahan | 623/6 |
| 5,123,921 | 6/1992 | Werblin et al. | 623/5 |
| 5,147,395 | 9/1992 | Willis | 623/6 |
| 5,192,319 | 3/1993 | Worst | 623/6 |
| 5,222,981 | 6/1993 | Werblin | 623/6 |
| 5,405,384 | 4/1995 | Silvestrini | 623/5 |
| 5,433,746 | 7/1995 | Namdaran et al. | 623/6 |
| 5,556,400 | 9/1996 | Tunis | 606/107 |

Primary Examiner—Michael Buiz
Assistant Examiner—Lien Nao
Attorney, Agent, or Firm—David P. Gordon; David S. Jacobson; Thomas A. Gallagher

[57] ABSTRACT

A flexible and transparent corneal endothelium protective device includes a relatively thin protective barrier portion, and a relatively thicker form-providing rim around the barrier portion. An access opening is provided through at least one of the rim and the barrier portion. The protective device is foldable for insertion through a surgical incision, is resilient such that it springs into shape once positioned in the eye, and is sufficiently flexible such that it may easily be removed through the incision in the eye near the completion of the surgical procedure. Various shapes are provided for the device. The protective device is inserted through the small incision and maneuvered into the space between the iris and the cornea and permitted to unfold. During surgery, instruments and other devices may be passed through the surgical incision and extend through an access opening of the protective device to operate on the lens. The intraocular protective device creates a protective barrier between the corneal endothelium and acoustic shock, instruments, other devices, and cataract fragments. As such, the intraocular protective device prevents damage to the fragile corneal endothelium. When the surgery is close to completion, but prior to closing the incision, the protective device is removed through the operating incision by grasping any portion of the device and pulling it through the incision.

22 Claims, 6 Drawing Sheets

CORNEAL ENDOTHELIUM PROTECTIVE DEVICE

BACKGROUND OF THE INVENTION

1. Field of the Invention

This invention relates broadly to intraocular devices and surgery. More particularly, this invention relates to intraocular devices used to protect the corneal endothelium during intraocular surgery.

2. State of the Art

The human eye is generally divided into three chambers, the anterior chamber, the posterior chamber, and larger vitreous space anterior of the retina. The anterior chamber includes a transparent and protective cornea as its front wall and the iris or the colored part of the eye as its posterior division. The iris has a pupil, a physiologically active opening in the center of the iris. The posterior chamber rests immediately behind the iris and the pupil and houses the normally transparent crystalline lens of the eye which transmits and focuses light onto the retina at the posterior aspect of the vitreous chamber. The iris separates the anterior chamber from the posterior chamber, and the pupil in the center of the iris regulates how much of the light passing through the cornea reaches the lens and the retina at the posterior aspect of the vitreous space. A cataract is an opacity of the normally transparent lens which obstructs vision. In order to restore vision, ophthalmic surgery is required to remove the cataract.

During ophthalmic surgery a small incision is made at the surgical limbus where the periphery of the cornea meets the sclera. A viscoelastic fluid is then provided through the incision and into the anterior chamber between the iris and the cornea to maintain proper pressure in the eye and prevent the collapse of the anterior chamber. The pupil is also dilated, either mechanically or pharmacologically. As the physician views the lens through the cornea and dilated pupil, instruments are passed through the incision and operated to break the opacities of the lens into fragments, typically using phacoemulsification. In phacoemulsification, a phaco needle is inserted into the cataractous lens and ultrasonically vibrated to carve away and emulsify the cataract. The emulsion is then aspirated out through an aspiration conduit in the phaco needle, while fluid is simultaneously irrigated into the eye from a fluid tube to maintain proper fluid pressure in the eye in the areas adjacent the lens. The natural lens is then supplanted, or supplemented, with an intraocular lens implanted either anterior or posterior the iris or within a capsular bag of the natural lens. The intraocular lenses described in U.S. Pat. No. 4,077,071 to Freeman, U.S. Pat. No. 4,573,998 to Mazzocco, U.S. Pat. No. 4,769,035 to Kelman, U.S. Pat. No. 5,129,319 to Worst, U.S. Pat. No. 5,258,025 to Federov et al., U.S. Pat. No. 5,433,746 to Namdaran, and U.S. Pat. No. 5,556,400 to Tunis are typical of the types of intraocular lenses used.

Throughout the cataract removal and/or intraocular lens implant procedure, multiple instruments may be manipulated within the anterior chamber at once. The operating physician must take great care to prevent any of the instruments from contacting the fragile underside of the cornea, the endothelium, as any damage to the endothelium is considered non-reversible; the cells of the endothelium are neither repairable nor easily replaced. In addition, great care is taken in trying to prevent fragmented pieces of the hard cataract from scratching the endothelium by quickly removing the cataract from the eye. Furthermore, great care must be taken during insertion of the replacement lens into the eye, as some intraocular replacement lenses can destroy endothelial cells if the replacement lens comes into contact with the cells. However, despite all of the care taken, endothelium damage is not uncommon during cataract surgery, as during phacoemulsification of the cataract, shards of the cataract can break off and hit the endothelium.

SUMMARY OF THE INVENTION

It is therefore an object of the invention to provide a device which offers protection to the corneal endothelium from instruments and debris in the eye during eye surgery.

It is a further object of the invention to provide a corneal endothelium protective device which permits easy access to the lens of the eye.

It is another object of the invention to provide a corneal endothelium protective device which does not obstruct a physician's view into the eye during surgery.

It is a also object of the invention to provide a corneal endothelium protective device which in easily insertable into the eye and removed therefrom.

In accord with these objects which will be discussed in detail below, a flexible and transparent corneal endothelium protective device is provided which can be inserted through a surgical incision and placed between the cornea and the iris. The device preferably has a relatively thin protective barrier portion, having outer and inner surfaces, and a relatively thicker form-providing rim around the barrier portion. In at least one of the rim and the protective barrier, an access opening is provided through which instruments and other devices, e.g., the intraocular lens, may be inserted into the eye. In one embodiment of the invention, the rim of the protective device is provided with projections which assist a physician in rotating the device once the device is placed within the eye so that the access opening is accessible for instruments and other devices to be passed therethrough. The corneal endothelium protective device is preferably molded from silicon, is foldable for insertion through the incision, is resilient such that it springs into shape once positioned in the eye, and is sufficiently flexible such that it may easily be removed through the incision in the eye near the completion of the surgical procedure.

According to a first preferred embodiment of the corneal endothelium protective device, the device is generally circular dome-shaped with a thin barrier portion and a more stable rim, the rim having a diameter of approximately 9–11.5 mm. The barrier portion is approximately 20–80 microns thick and 5–11 mm in diameter and the rim is approximately 0.3–1 mm thick. The access opening is preferably provided through a section of the barrier portion, but may alternatively or additionally be provided through a section of the rim. The access opening can take any of many shapes. According to other embodiments of the invention, dome shapes other than circular are provided to the device, e.g., U-shaped, wishbone-shaped, and triangular domes or tents.

In practice, the corneal endothelium protective device is provided with a small amount of a viscoelastic material on its outer (upper) surface, gripped with an insertion device, and folded into a relatively small size, e.g., 2–4 mm wide and 0.5–2 mm in height. The protective device is inserted through the small incision and maneuvered into the space between the iris and the cornea and permitted to unfold. The rim of the protective device rests preferably on the floor of the anterior chamber at the angle of the iris, i.e., where the floor of the anterior chamber surrounding the iris meets the cornea. The viscoelastic material on the outer surface of the barrier portion of the protective device separates the device from the endothelium of the cornea. Viscoelastic material is also injected between the inner surface of the barrier portion and the floor of the anterior chamber to "fill" the protective device. The device protects the endothelial cells at the central portions of the cornea; i.e., the optical portions of the cornea, and the viscoelastic material provides stability to the incised anterior chamber. The protective device, once inserted, may be rotated by the operating physician to orient the access opening adjacent the surgical incision. During surgery, instruments and other devices, e.g. an intraocular lens, may be passed through the surgical incision and the access opening of the protective device to operate on the cataract and/or lens of the eye.

It will be appreciated that during surgery the intraocular protective device creates a protective barrier between the corneal endothelium and instruments, other devices, acoustic energy, cataract fragments, and fluid. As such, the intraocular protective device prevents damage to the fragile corneal endothelium. When the surgery is near completion, but prior to closing the incision, the protective device may be removed through the operating incision by grasping any portion of the device and pulling it through the incision.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
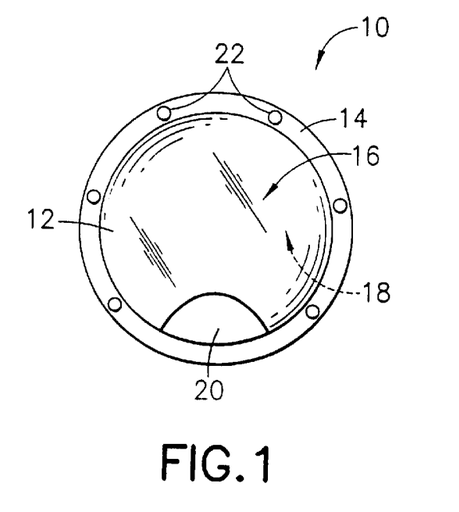
FIG. 1 is a top view of a first embodiment of a corneal endothelium protective device according to the invention.
Figure 2:
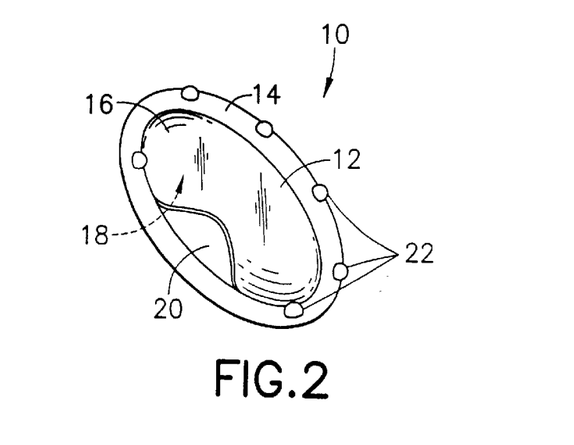
FIG. 2 is a perspective view of the corneal endothelium protective device of FIG. 1.

Turning now to FIGS. 1 and 2, a corneal endothelium protective device 10 according to a first embodiment of the invention is shown. The device 10 is generally circular dome-shaped and has a relatively thin central protective barrier portion 12, having an outer (upper) surface 16 and a inner (lower) surface 18, and a relatively thicker form-providing rim 14 surrounding the barrier portion. The protective device preferably has an outer rim diameter of approximately 9 mm to 11.5 mm, the barrier portion 12 is preferably approximately 20–80 microns thick and 5–11 mm in diameter, and the rim 14 is preferably approximately 0.3–1 mm thick at its thickest portion. An access opening 20 is provided in the barrier portion 12 through which instruments and other devices, e.g., a folded intraocular lens, may be inserted into the eye, as described below. The access opening is preferably provided along a 30°–70° arc of the generally circular rim. Preferably, the rim 14 is provided with a plurality of small projections 22 which assist a physician in rotating the device once the device is placed within the eye so that the access opening is accessible for devices at the distal ends of instruments to be passed therethrough.

The corneal endothelium protective device is preferably transfer molded from silicon, is foldable for insertion through a surgical incision, is resilient such that it springs into shape once positioned in the eye, and is sufficiently flexible such that it may easily be removed through the incision in the eye upon the completion of a surgical procedure. In addition, the corneal endothelium protective device is substantially transparent, permitting an operating physician to clearly view through the protective device the anterior chamber of the eye, the distal ends of instruments, and other devices located in the anterior chamber.

Figure 3:
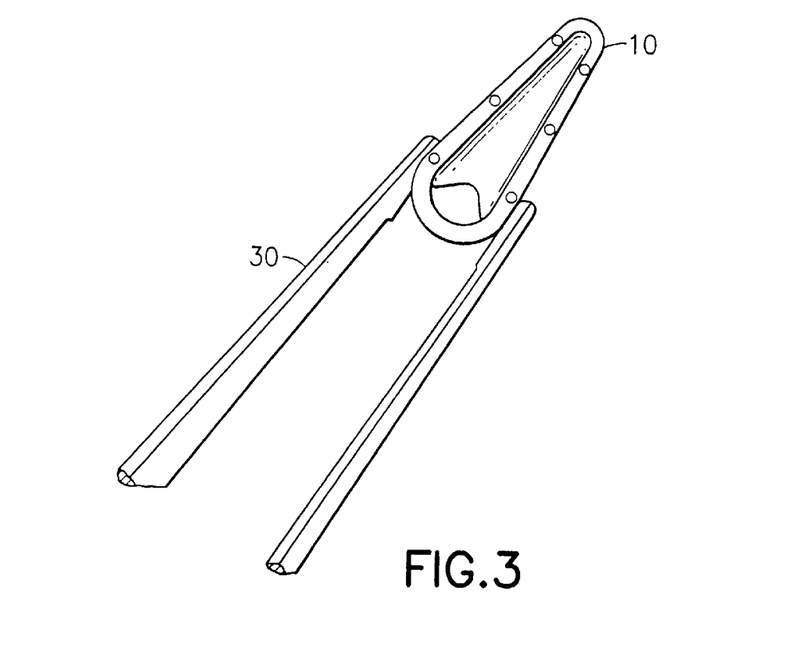
FIG. 3 is a perspective view of the corneal endothelium protective device according to the invention being compressed by an insertion device.
Figure 4:
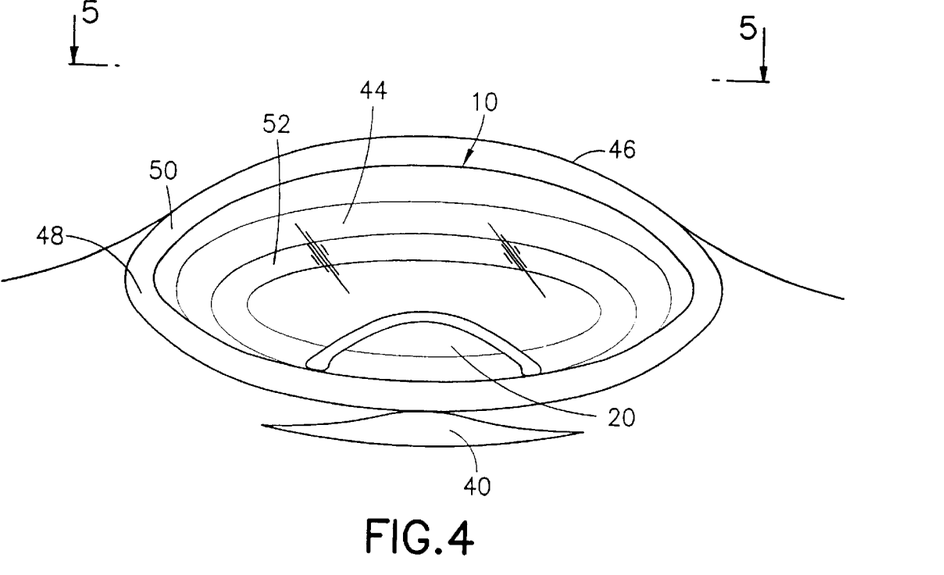
FIG. 4 is a perspective view of a corneal endothelium protective device inserted into an eye.
Figure 5:
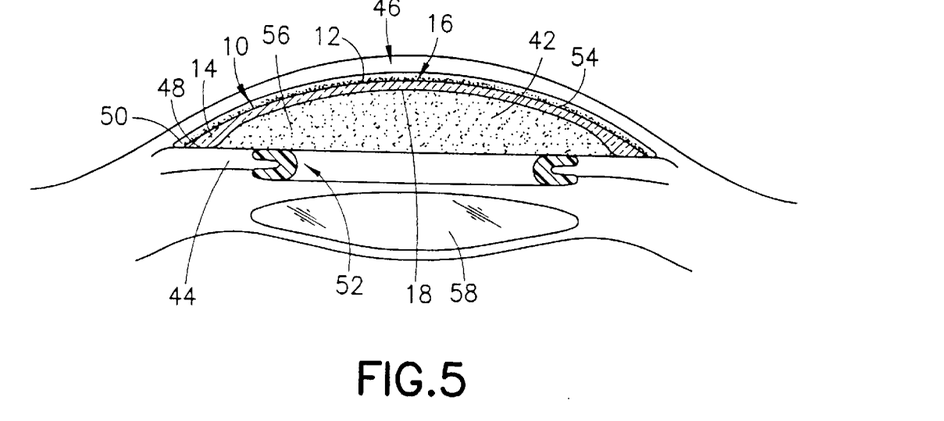
FIG. 5 is a cross section through line 5–5 in FIG. 4.

In practice and with reference to FIGS. 3 through 5, the outer surface 16 of the barrier portion 12 of the corneal endothelium protective device 10 is provided with a small amount of viscoelastic material 54, e.g., Healon™ which is sold by Pharmacia of Sweden. The protection device is then gripped with an insertion device 30 and folded into a relatively small size, e.g., 2.5 mm in width, in generally the same manner as an intraocular lens is folded for insertion. The protective device 10 is next inserted through a small incision 40, approximately 2.8 mm to 3.4 mm wide, at the surgical limbus, and maneuvered into the anterior chamber 42, between the iris 44 and the cornea 46. The protective device 10 is then permitted to unfold such that the rim 14 of the protective device rests preferably on the floor 48 of the anterior chamber 42 at the angle 50 of the iris, i.e., where the floor of the anterior chamber surrounding the iris meets the cornea. Where a mechanical iris dilator 52 is used, e.g., a Graether Pupil Expander™, sold by Eagle Vision of Memphis, Tenn., the protective device is designed to seat outside the periphery of the mechanical iris dilator. Viscoelastic material 56 is also injected between the inner surface 18 of the barrier portion 12 and the floor 48 of the anterior chamber. The viscoelastic material 54 applied to the outer surface of the barrier portion separates the protection device form the corneal endothelium, and the injected viscoelastic material 56 "fills" the tent-like shape of the protective device. The protective device protects the endothelial cells at the central portions of the cornea; i.e., the optical portions of the cornea, and the viscoelastic material provides stability to the incised anterior chamber. If the access opening 20 is not already directed toward the surgical incision 40, the operating physician, preferably using the projections 22, rotates the "inflated" protective device to move the access opening 20 adjacent the incision. During surgery, instruments may be passed through the surgical incision 40 and through the access opening 20 of the protective device to operate on the lens 58. Similarly, where the lens 58 is to be replaced or supplemented, other devices such as an artificial intraocular lens (not shown) may be passed through the surgical incision 40 and through the access opening 20.

It will be appreciated that during surgery the corneal endothelium protective device creates a protective barrier between the corneal endothelium and acoustic shock, instruments, irrigating fluid, cataract fragments, and other devices passing in and out of the eye. The device, thereby, prevents damage to the fragile corneal endothelium. When the surgery is almost complete, but prior to closing the incision, the protective device is removed. The device may be pulled through the operating incision by grasping any portion of the device and pulling it through the incision.

Figure 6:
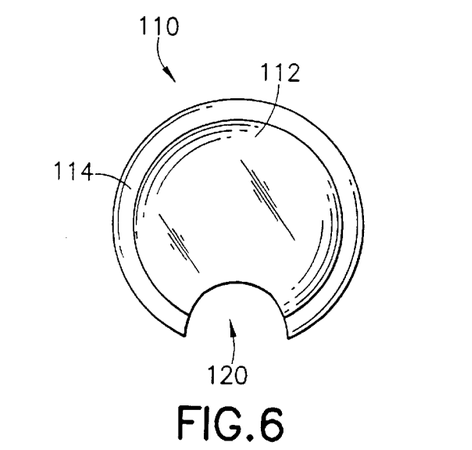
FIG. 6 is a top view of a second embodiment of a corneal endothelium protective device according to the invention.
Figure 7:
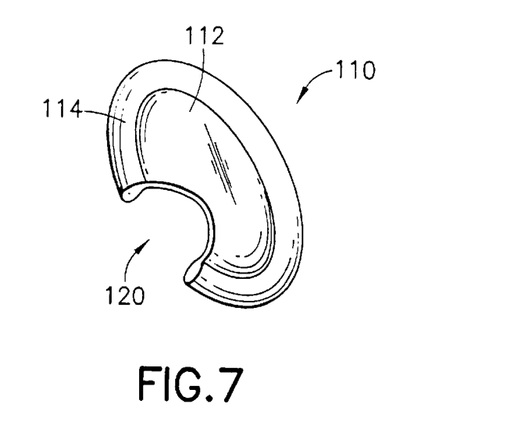
FIG. 7 is a perspective view of the corneal endothelium protective device of FIG. 6.

Turning now to FIGS. 6 and 7, a second embodiment of a corneal endothelium protective device 110, substantially similar to the first embodiment (with like parts having similar numbers incremented by 100), is shown. The device 110 is generally circular dome-shaped and has a protective barrier portion 112 and a rim 114. An access opening 120 is provided by an opening in the barrier portion 112 and a discontinuity of the rim 114.

Figure 8:
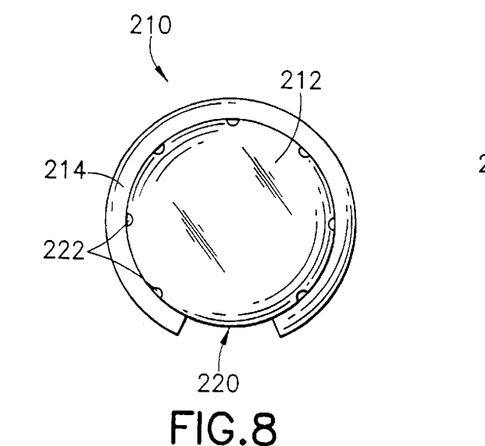
FIG. 8 is a top view of a third embodiment of a corneal endothelium protective device according to the invention.
Figure 9:
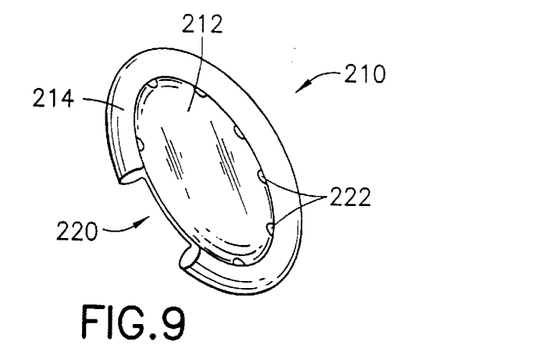
FIG. 9 is a perspective view of the corneal endothelium protective device of FIG. 8.

Referring now to FIGS. 8 and 9, a third embodiment of a corneal endothelium protective device 210, substantially similar to the first embodiment (with like parts having similar numbers incremented by 200), is shown. The device 210 is generally circular dome-shaped and has a protective barrier portion 212 and a rim 214 partially surrounding the barrier portion 212. An access opening 220 is provided at the periphery of the device, where the barrier portion 212 is not surrounded by the rim 214; i.e., where the rim is discontinuous. Small holes 222 are provided in the barrier portion to assist the physician in orienting the device.

Figure 10:
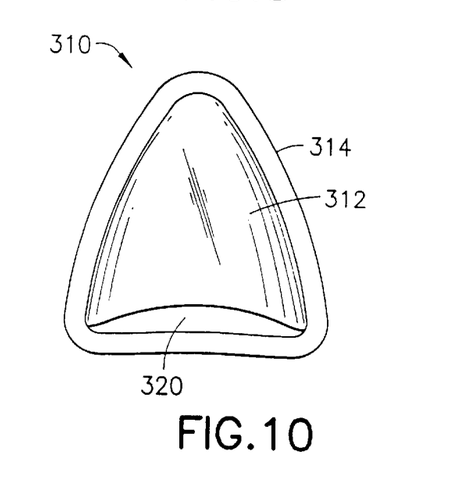
FIG. 10 is a top view of a fourth embodiment of a corneal endothelium protective device according to the invention.
Figure 11:
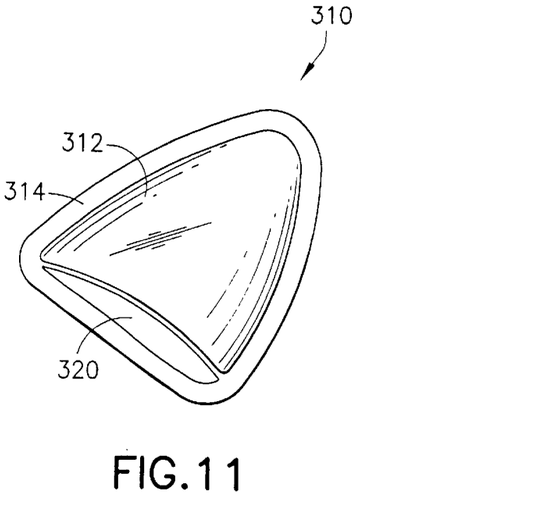
FIG. 11 is a perspective view of the corneal endothelium protective device of FIG. 10.

Turning now to FIGS. 10 and 11, a fourth embodiment of a corneal endothelium protective device 310, substantially similar to the first embodiment (with like parts having similar numbers incremented by 300), is shown. The device 310 is generally triangular dome-shaped, and has a protective barrier portion 312 and a rim 314 surrounding the barrier portion 312. An access opening 320 is provided by a disjunction of the rim 314 from the barrier portion 312 along one of the sides of the device.

Figure 12:
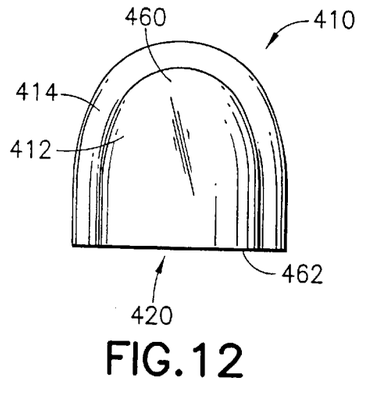
FIG. 12 is a top view of a fifth embodiment of a corneal endothelium protective device according to the invention.
Figure 13:
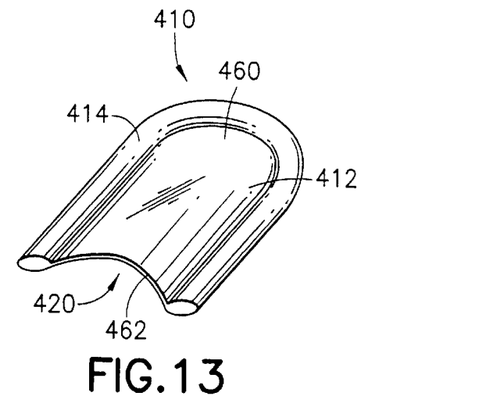
FIG. 13 is a perspective view of the corneal endothelium protective device of FIG. 12.

Referring now to FIGS. 12 and 13, a fifth embodiment of a corneal endothelium protective device 410, substantially similar to the first embodiment (with like parts having similar numbers incremented by 400), is shown. The device 410 is generally a U-shaped tent, and has a protective barrier portion 412 and a U-shaped rim 414 surrounding the curved portion 460 of the barrier portion. When the device is "inflated", i.e., when the device is inserted in the eye and the anterior chamber is filled with viscoelastic material, the side 462 of the barrier portion 412 not provided with the rim 414 is lifted away from the incision and thereby provides an access opening 420.

Figure 14:
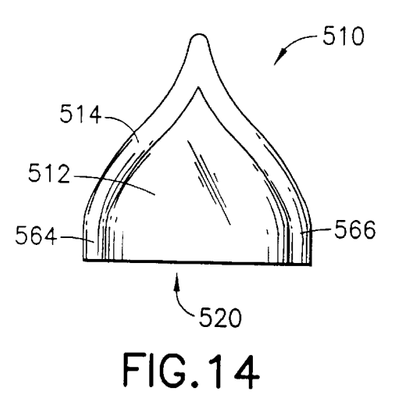
FIG. 14 is a top view of a sixth embodiment of a corneal endothelium protective device according to the invention.
Figure 15:
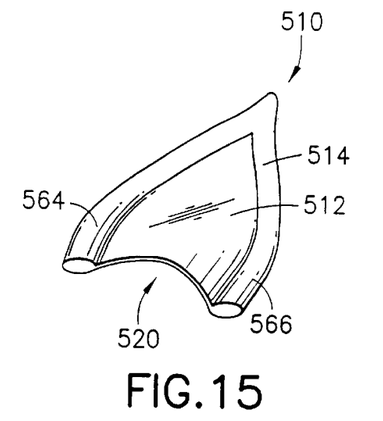
FIG. 15 is a perspective view of the corneal endothelium protective device of FIG. 14.

Turning now to FIGS. 14 and 15, a sixth embodiment of a corneal endothelium protective device 510, substantially similar to the fifth embodiment (with like parts having similar numbers incremented by 400), is shown. The device 510 is generally a wishbone-shaped tent, and has a protective barrier portion 512 and a rim 514 divided into two arms 564, 566 surrounding a portion of the barrier portion. The portion of the barrier portion not surrounded by the arms 564, 566 acts as an access opening 520.

Figure 16:
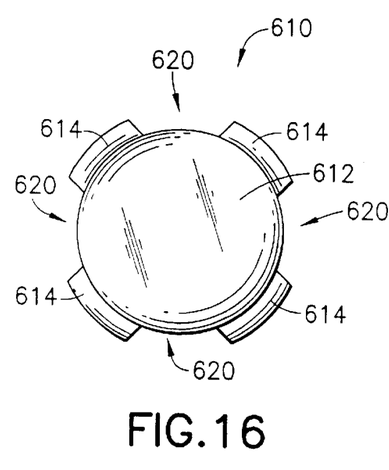
FIG. 16 is a top view of a seventh embodiment of a corneal endothelium protective device according to the invention.
Figure 17:
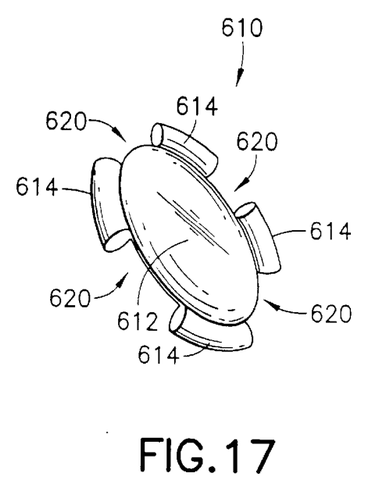
FIG. 17 is a perspective view of the corneal endothelium protective device of FIG. 16.

Referring now to FIGS. 16 and 17, a seventh embodiment of a corneal endothelium protective device 610, substantially similar to the first embodiment (with like parts having similar numbers incremented by 600), is shown. The device 610 is generally circular dome-shaped and has a protective barrier portion 612 and a discontinuous rim 614 partially surrounding the barrier portion 612. Access openings 620 are provided at the periphery of the device, where the barrier portion 612 is not surrounded by the rim 614; i.e., where the rim is discontinuous.

Figure 18:
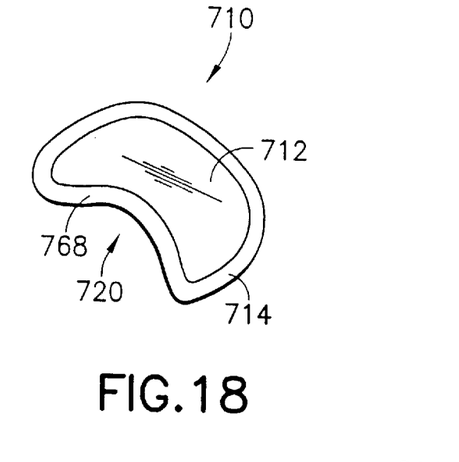
FIG. 18 is a perspective view of an eighth embodiment of a corneal endothelium protective device.
Figure 19:
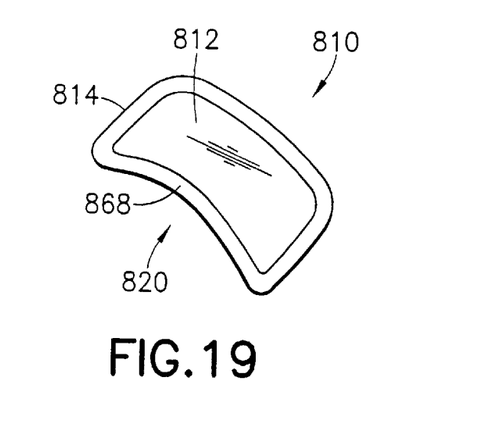
FIG. 19 is a perspective view of a ninth embodiment of a corneal endothelium protective device.

Turning now to FIG. 18, an eighth embodiment of a corneal endothelium protective device 710, substantially similar to the first embodiment (with like parts having similar numbers incremented by 700), is shown. The protective barrier portion 712 of the device is generally circular shaped, and the rim 714 follows a three dimensional curve and has a raised portion 768 which provides an access opening 720. The rim may also be raised at two locations, providing a saddle shape to the device, or at more than two locations. In addition, other general shapes may be provided to a device having a three-dimensional rim. For example, and with reference to a ninth embodiment of a corneal endothelium protective device 810 as shown in FIG. 19, the protective barrier portion 812 of the device is generally rectangular in shape and has a bordering rim 814 which has a raised portion 868 forming an access opening 820.

Figure 20:
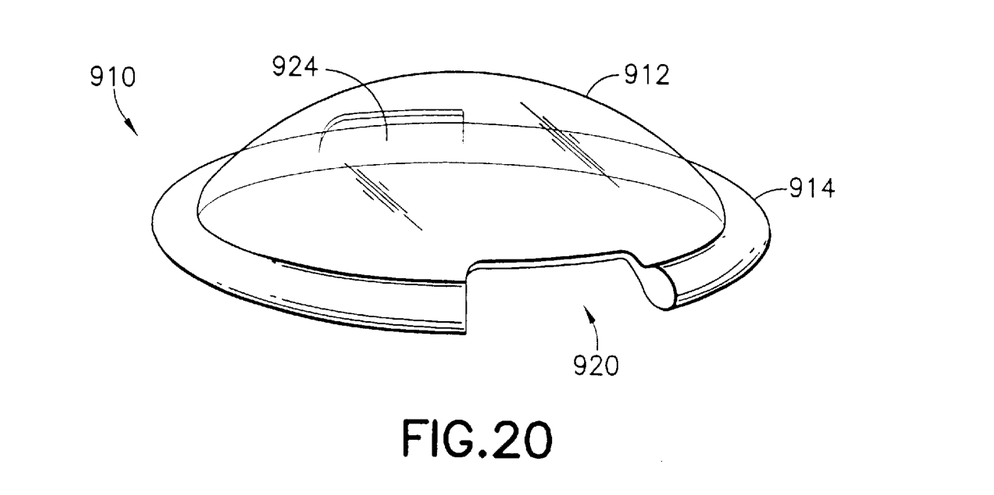
FIG. 20 is a perspective view of a tenth embodiment of a corneal endothelium protective device.

Referring to FIG. 20, a tenth embodiment of a corneal endothelium protective device 910, substantially similar to the second embodiment (shown in FIGS. 6 and 7), is shown. The device 910 is generally circular dome-shaped and has a protective barrier portion 912 and a rim 914. An access opening 920 is provided by an opening in the barrier portion 912 and a discontinuity of the rim 914. A vent opening 924 is also provided in the barrier portion, preferably opposite the access opening 920. The vent opening 924 permits more uniform dispersion of a viscoelastic material, described above, and also provides an entryway for secondary instrument (as shown in FIG. 21 with respect to the eleventh embodiment).

Figure 21:
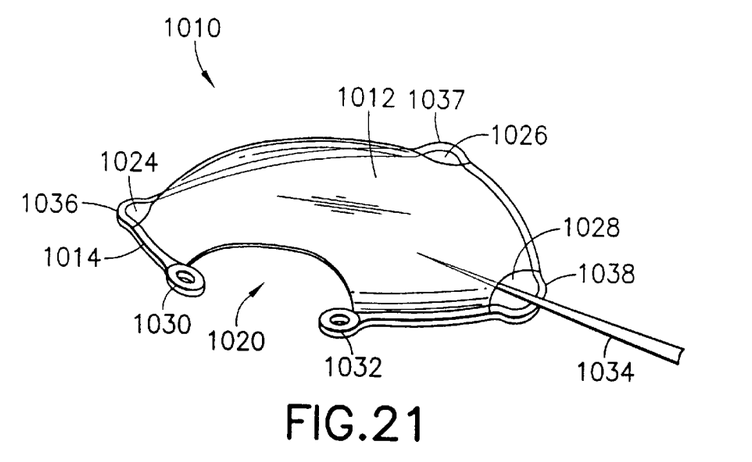
FIG. 21 is a perspective view of an eleventh embodiment of a corneal endothelium protective device.
Figure 22:
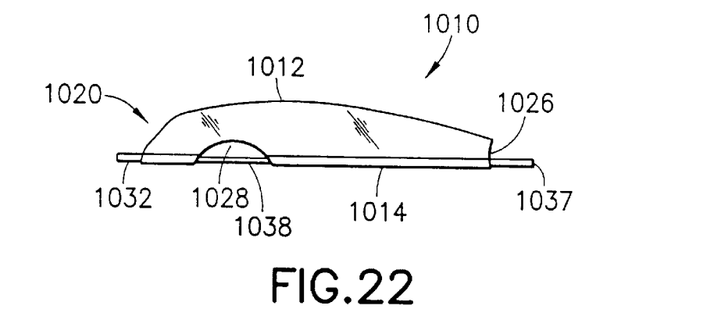
FIG. 22 is a side view of the corneal endothelium protective device shown in FIG. 21.

Turning to FIGS. 21 and 22, an eleventh embodiment of a corneal endothelium protective device 1010, substantially similar to the second embodiment (shown in FIGS. 6 and 7), is shown. The device 1010 includes a protective barrier portion 1012 coupled to a flexible haptic rim 1014, and an access opening 1020 formed by the barrier portion and the rim. Each of two ends of the rim 1014 are provided with a ring-shaped tab 1030, 1032 which assist in insertion, manipulation, and removal of the device 1010. The device is also provided with three vent openings 1024, 1026, 1028, preferably located approximately 120° relative to each other around the perimeter of the device. The vent openings 1024, 1026, 1028 permit uniform dispersion of a viscoelastic material, e.g., Healon™, and provide entry for secondary instruments, e.g., instrument 1034. The haptic rim at 1036, 1037, 1038 preferably expands through the vent openings and provides a means for three point contact in the angle of the iris.

Figure 23:
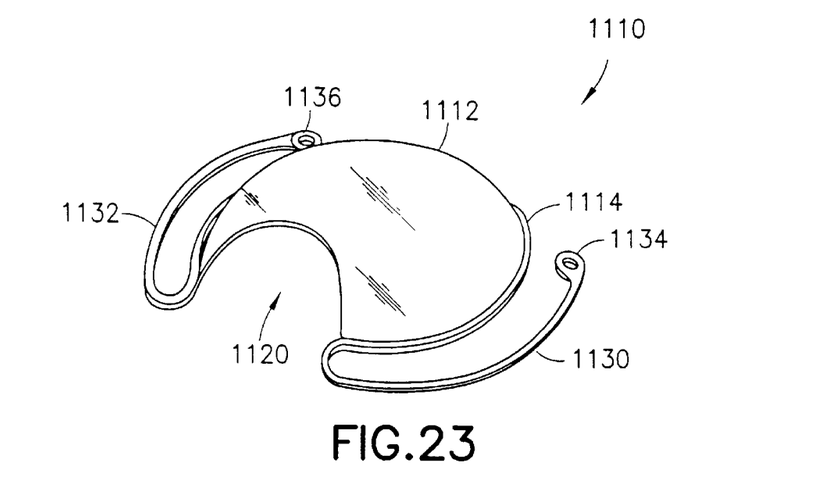
FIG. 23 is a perspective view of a twelfth embodiment of a corneal endothelium protective device.

Referring to FIG. 23, a twelfth embodiment of a corneal endothelium protective device 1110, substantially similar to the second embodiment (shown in FIGS. 6 and 7), is shown. The device 1110 is generally circular dome-shaped and has a protective barrier portion 1112 and a rim 1114. An access opening 1120 is provided by an opening in the barrier portion 1112. Spring-tensioned haptics 1130, 1132, preferably unitarily formed with the rim 1114, are provided for holding the device centered in the anterior chamber. The ends of the haptics 1130, 1132 are preferably formed with ring-shaped tabs 1134, 1136 for insertion, manipulation, and removal of the device.

There have been described and illustrated herein several embodiments of a corneal endothelium protective device and a method of inserting the same into the eye. While particular embodiments of the invention have been described, it is not intended that the invention be limited thereto, as it is intended that the invention be as broad in scope as the art will allow and that the specification be read likewise. Thus, while particular shapes for the device have been disclosed, it will be appreciated that other shapes can be used as well, as long as the resulting device protects the endothelium of the cornea when inserted into the eye. Also, while the protective device has been described as dome-shaped and having an outer surface and a inner surface, it will be appreciated that the device may be made in a symmetrical disc shape or other substantially flat shape, such that either surface may be the outer or inner surface, depending upon the orientation of the protective device. In addition, while devices of particular shapes have been described with respect to having an access opening in particular locations, it will be appreciated that any shaped device may have any of the access openings described, and that the access openings may be larger or smaller than particularly described. Moreover, while one embodiment has been shown to have a plurality of access openings, it will be appreciated that each of the other embodiments may likewise have a plurality of access openings formed in the same manner as described with respect to that embodiment or any other embodiment. Furthermore while silicon has been disclosed as the preferred material for construction, it will be understood that other materials, e.g., other transparent polyelastomers to other suitable materials, can be used. Moreover, while the rim of the protective device has been disclosed as being relatively thicker than the barrier portion of the device, it will be appreciated that the rim and the barrier portion may be substantially the same thickness. In addition, while the barrier portion and the rim of the protective device have been disclosed as preferably being integrally molded, it will be appreciated that the barrier portion and rim may be made from one or two pieces. Also, while a plurality of projections along the rim or holes in the barrier portion have been disclosed for orienting the device once the device is located in the anterior chamber, it will be recognized that such projections or holes only assist the physician, and are not required. Furthermore, as an alternative to or in addition to projections and holes, indentations, other orienting means, or indications of orientation may be used, provided to either of the barrier portion and the rim. In addition, while a viscoelastic material has been disclosed for creating a barrier between the cornea and the device, and for filling the anterior chamber under the inner side of the barrier portion of the device, it will be appreciated that other fluids, e.g., gases, water, and aqueous solutions, can also be used. Also, while the viscoelastic material has been described as being coated on the outer surface of the barrier portion prior to insertion of the protective device into the eye, it will be appreciated that fluid may be provided between the outer surface of the protective device and the cornea after the protective device has been positioned in the anterior chamber. Moreover, while particular dimensions have been disclosed, it will be appreciated that the device may be provided with other dimensions, on the condition that the device is sized to seat at the angle of an iris. Furthermore, while a particular order has been provided with respect to inserting a mechanical iris dilator and inserting the device of the invention, it will be appreciated that another order can be similarly used. Moreover, while the device has been described with respect to being used during cataract surgery, it will be appreciated that the device has use in other eye surgical procedures where potentially damaging contact with the corneal endothelium may occur, such as corneal transplants or other anterior segment procedures. It will therefore be appreciated by those skilled in the art that yet other modifications could be made to the provided invention without deviating from its spirit and scope as so claimed.

What is claimed is:

1. A corneal endothelium protective device for insertion through a surgical incision and into an anterior chamber of an eye between a cornea and an iris and for preventing damage to a corneal endothelium during surgery utilizing a surgical instrument, comprising:

a flexible central portion and a resilient rim connected to said central portion, said central portion and said rim sized to fit within the anterior chamber of the eye, at least one of said central portion and said rim defining an access opening which permits at least a portion of the surgical instrument to extend therethrough, under said corneal endothelium protective device, and into the anterior chamber of the eye.

2. A corneal endothelium protective device according to claim 1, wherein:

said access opening is provided in said central portion.

3. A corneal endothelium protective device according to claim 2, wherein:

said rim is generally circular and said access opening is provided in said central portion at an approximately 30°–70° arc along said rim.

4. A corneal endothelium protective device according to claim 1, wherein:

said access opening is a discontinuity of said rim.

5. A corneal endothelium protective device according to claim 1, wherein:

said access opening is provided by a disjunction between said central portion and said rim.

6. A corneal endothelium protective device according to claim 1, wherein:

said central portion is a dome being generally one of circular, triangular, U-shaped, and wishbone-shaped.

7. A corneal endothelium protective device according to claim 1, wherein:

said device is made of silicon.

8. A corneal endothelium protective device according to claim 1, wherein:

said device is formed of a material and said material is thicker at said rim than at a said central portion.

9. A corneal endothelium protective device according to claim 1, wherein:

said rim is approximately 0.3–1 mm thick and said central portion is approximately 20–80 microns thick.

10. A corneal endothelium protective device according to claim 1, wherein:

a largest dimension of said device is less than 12 mm.

11. A corneal endothelium protective device according to claim 1, further comprising:

orienting means provided at one of said central portion and said rim for rotationally orienting said device.

12. A corneal endothelium protective device according to claim 11, wherein:

said orienting means is at least one ring-shaped tab coupled to said rim.

13. A corneal endothelium protective device according to claim 1, wherein:

said central portion defines at least one secondary opening.

14. A corneal endothelium protective device according to claim 1, further comprising:

means for maintaining a position of said central portion relative to said iris.

15. A corneal endothelium protective device according to claim 14, wherein:

said means for maintaining a position is at least one spring-tensioned haptic.

16. A corneal endothelium protective device for insertion through a surgical incision and into an anterior chamber of an eye between a cornea and an iris and for preventing damage to a corneal endothelium during surgery utilizing a surgical instrument, comprising:

a flexible barrier sized to fit within the anterior chamber of the eye, said flexible barrier defining an access opening which permits at least a portion of the surgical instrument to extend therethrough, under said corneal endothelium protective device, and into the anterior chamber of the eye.

17. A corneal endothelium protective device according to claim 16, wherein:

said flexible barrier is transparent and made from silicon.

18. A corneal endothelium protective device according to claim 16, wherein a central portion of said flexible barrier has a thickness of less than 1 mm.

19. A method of protecting a corneal endothelium during eye surgery, comprising:

a) inserting a protective barrier through an incision and into a anterior chamber of an eye between a cornea and the iris;

b) positioning the protective barrier adjacent one of an iris of the eye and the floor of the anterior chamber; and c) providing a fluid into a space between the protective barrier and the floor of the anterior chamber.

20. A method according to claim 19, further comprising:

d) providing a fluid between the protective barrier and the cornea.

21. A method according to claim 19, wherein:

said protective barrier has a flexible central portion and a resilient rim integral with said central portion.

22. A method according to claim 19, wherein:

said protective barrier further includes an access opening through which a portion of a surgical instrument can extend.

* * * * *